(12) United States Patent
Codignola

(10) Patent No.: US 7,335,797 B2
(45) Date of Patent: Feb. 26, 2008

(54) PROCESS FOR THE SYNTHESIS OF CUMENE HYDROPEROXIDE

(75) Inventor: Franco Codignola, Milan (IT)

(73) Assignee: Eurotechnica Development & Licensing S.p.A., Milan (IT)

( * ) Notice: Subject to any disclaimer, the term of this patent is extended or adjusted under 35 U.S.C. 154(b) by 0 days.

(21) Appl. No.: 10/507,227

(22) PCT Filed: Mar. 14, 2002

(86) PCT No.: PCT/IT02/00157

§ 371 (c)(1),
(2), (4) Date: May 11, 2005

(87) PCT Pub. No.: WO03/076381

PCT Pub. Date: Sep. 18, 2003

(65) Prior Publication Data

US 2006/0014985 A1    Jan. 19, 2006

(51) Int. Cl.
*C07C 409/00* (2006.01)

(52) U.S. Cl. .................................... 568/558
(58) Field of Classification Search ............. 568/558
See application file for complete search history.

(56) References Cited

U.S. PATENT DOCUMENTS 3,171,860 A * 3/1965 Codignola ................. 568/574

4,153,635 A * 5/1979 Wu et al. ................... 568/574

FOREIGN PATENT DOCUMENTS

| GB | 970 945 | 9/1964 |
|---|---|---|
| WO | WO 95 04717 | 2/1995 |

OTHER PUBLICATIONS

Boncheva et al., Oxidation of Cumene in the Presence of Anion Exchange Resins, Neft i Khimiya, 1977, 11, 15-18.*

* cited by examiner

*Primary Examiner*—Yvonne (Bonnie) Eyler
*Assistant Examiner*—Chukwuma Nwaonicha
(74) *Attorney, Agent, or Firm*—Ohlandt, Greeley, Ruggiero & Perle, L.L.P.

(57) ABSTRACT

This invention refers to a process for the synthesis of cumene hydroperoxide and to the product thus obtained.

More in particular, this invention refers to a process for the production of cumene hydroperoxide by oxidating cumene with oxygen, where this process is run in the presence of a basic medium insoluble in the reaction environment, and such as not to release inorganic cations to the reaction environment. Such a basic medium is preferably a pyridinic resin.

The cumene hydroperoxide thus obtained, characterized by the fact of being free of inorganic cations, is a further object of the invention.

14 Claims, 2 Drawing Sheets

PROCESS FOR THE SYNTHESIS OF CUMENE HYDROPEROXIDE

This invention refers to a process for the synthesis of cumene hydroperoxide and the product thus obtained. In particular, the process of this invention shapes up as an industrial preparation of cumene hydroperoxide.

As known, cumene hydroperoxide is the starting material utilized for the production of phenol and acetone. At this time, over 90% of the phenol produced in the world is synthesized by decomposition of cumene hydroperoxide, a decomposition which simultaneously yields a mole of acetone per mole of phenol in accordance with the following reaction:

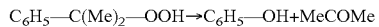

However, cumene hydroperoxide has further uses, for instance as an initiator of radicals, which make it essential to synthesize it with a high selectivity, that is by minimizing the formation of possible byproducts which would hinder its specific application. In particular, the use of cumene hydroperoxide as an initiator of radicals can be prevented by an incidental partial decomposition of the hydroperoxide to phenol, a reaction known to be catalyzed by acids.

Cumene hydroperoxide is prepared by oxidizing cumene with oxygen in a liquid phase:

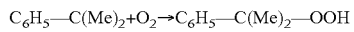

The main byproducts of this reaction are acetophenone, dimethylphenylcarbinol and formic acid.

The latter in particular has, because of its acidity, the capability of catalyzing a partial decomposition of cumene hydroperoxide to phenol, which even if present in small amounts blocks the further oxidation of cumene with the result that the reaction is interrupted at an unacceptably low percentage of conversion. This drawback is particularly noticeable in an industrial process, in which the conversion of cumene to hydroperoxide is generally limited to a percentage of 20-40% and the unreacted cumene is recycled to the oxidation reactor. In this case, the phenol tends to accumulate in the reactor, thus shortly inhibiting the continuation of the oxydation.

It is known that in order to neutralize the formic acid byproduct aqueous solutions of sodium salts with organic acids are introduced into the cumene mixture so as to buffer the reaction environment. An alternative employed for the same purpose was that of using the sodium salt of the same cumene hydroperoxide under anhydrous conditions (U.S. Pat. No. 3,171,860 in the name of F. Codignola). On the other hand, the process in use provides for feeding the oxidation reactor with cumene and caustic soda in a concentrated aqueous solution, so as to maintain a pH of an adequately high level to prevent initiating the decomposition of the hydroperoxide.

However, even under these conditions the decomposition of cumene hydroperoxide to phenol is not eliminated and depends both on the reaction temperature and on the concentration of the cumene hydroperoxide, which gradually rises as the oxidation proceeds. This reaction kynetic has made it necessary to perform the process in several separate reactors (for instance in three reactors) arranged in series and in which the oxidation is carried out at gradually decreasing temperatures (about 110° C. in the first reactor, about 100° C. in the second reactor and about 90° C. in the subsequent reactors), that is inversely proportional to the hydroperoxide concentration. In this manner, the reaction's selectivity toward the desired product passed from about 80-85% (for a reactor at a single temperature of 110° C.) to about 90% by using several reactors in series as described above, and thus with a substantial reduction of the byproducts. This has obviously caused a considerable increase of the investments needed to establish such plants, even in terms of their size.

A further disadvantage of the process in the known art is that the reaction mix leaving the oxidation reactors must be washed with water in order to remove the inorganic cations and their salts formed during the reaction. Apart from being expensive, this operation also causes the passing of a certain quantity of the produced cumene hydroperoxide into the water phase, which would be lost if it were not extracted with fresh cumene and then recycled to the oxidation reactor. The washwaters must therefore be neutralized and disposed of as wastes, an operation which further boosts the costs of the entire process.

Some industrial processes provide for performing the oxidation phase while using bases in an aqueous solution. In these processes it may not be necessary to provide for a washing phase at the reactor exit, as the salts are passing directly into an aqueous phase in the reaction environment. Provision must however be made for decanting and separating the aqueous phase downstream of the reactor, which will at any rate fail to eliminate the drawbacks mentioned above in connection with the usage of water.

However, the cumene hydroperoxide treated in this manner still contains a small yet uneliminable percentage of cations (typically sodium, potassium or ammonium, depending on the basic agent employed in the oxidation), and a residual percentage of water. The presence of water, in particular, hinders the subsequent stage of concentrating the cumene hydroperoxide and of recovering the unreacted cumene for distillation. The product mixture must in fact be preconcentrated under vacuum at 85-95° C. to eliminate the residual water before transferring it to the thin bed concentrator (type LUWA, BUSS or the like) operating at pressures of about 1 mm Hg, and thus finally obtaining a concentrate of 85-95% of cumene hydroperoxide.

As mentioned above, the product thus obtained contains non negligeable amounts of inorganic cations. The presence of such cations is disadvantageous in running the subsequent decomposition reaction to produce phenol and acetone, as it interferes with the functionality of any acid resins which could effectively be employed as decomposition catalysts. This consideration has limited the choice of traditional inorganic acids as acid catalysts, in particular of sulfuric acid, with the ensuing problems of safe usage and disposal associated with them.

The above makes it evident that there is a broad demand for a process of synthesizing cumene hydroperoxide capable of solving the mentioned disadvantages of the processes of the known art.

The problem underlying this invention is therefore to make available a process for the synthesis of cumene hydroperoxide capable of overcoming such disadvantages.

This problem is solved by a process for the synthesis of cumene hydroperoxide as outlined in the attached claims.

The process of the invention provides for oxidizing cumene with oxygen in an anhydrous liquid phase, in the presence of a basic medium stable and insoluble in the reaction environment, where said basic medium is such as not to release inorganic cations to the reaction environment. A preferred basic medium is a basic resin:

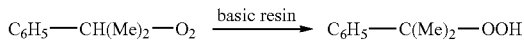

Cumene is generally used as such, without a need to add solvents.

The oxygen may be used in pure form or in a mixture with other gases of a preferably inert kind. For instance, a normally employed oxidizing agent is air. The reaction is preferably run at relative pressures in the range of 0.5 to 10 bar.

The basic resin is preferably a pyridinic resin. More preferably, it is chosen from the group comprising reticulated poly-4-vinylpyridin (a polymer of 4-ethenylpyridin with diethenylbenzene, CAS RN 9017-40-7, formula I), high porosity reticulated poly-4 vinylpyridin (CAS RN 9017-40-7, formula I), and a polymer of 4-ethenylpyridine with diethenylbenzene and ethenylethylbenzene quaternarized with methyl chloride (formula II):

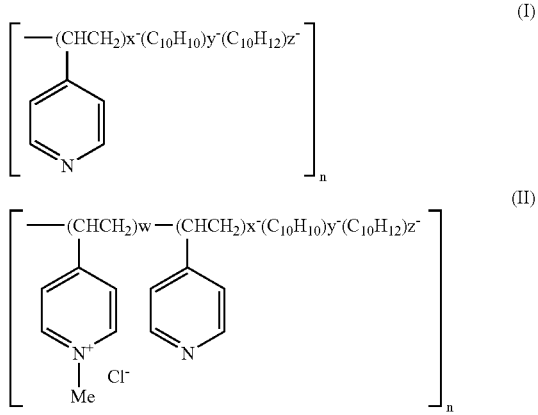

Such resins are commercial products and are for instance known under the name REILLEX™ 402-I, REILLEX™ 425, REILLEX™ HP, REILLEX™ HPQ and REILLEX™ 402 of the Reillex company. These resins are insoluble in water, in acids, bases and organic solvents and resistant to both high temperatures (over 220° C.) and oxidation with oxygen.

The basic medium may be used in suspension or be placed in appropriate baskets so that this basic medium is in contact with the reaction environment. In the latter case the separation of the basic medium from the reaction medium and its recovery at the conclusion of the process is easier. It is moreover possible to avoid that the insoluble basic medium, in particular the resin, crumbles to the point of forming a dust at the reactor's agitating conditions.

The usage is preferably between 1 and 60 g of basic medium for every kg of cumene, and more preferably between 10 and 25 g of basic medium for every kg of cumene.

The cumene may commonly be obtained by allowing benzene and propylene to react in the presence of acidic condensing agents such as AlCl3, sulphuric acid, BF3 or phosphoric acid supported on fossil flour or on zeolites of various type.

The oxidation reaction is generally performed at a temperature in the range from 60° C. to 150° C., preferably from 90° C. to 115° C. and for reaction times comprised between 30 minutes and 10 hours, preferably between 1 hour and six hours, at any rate until the conversion of cumene to hydroperoxide is between 5% and 40%, preferably between 20% and 25%.

The reaction may be performed both in a single reactor at a temperature around 110° C. as in two or more reactors in series, operating at decreasing temperatures. When using three reactors in series, for instance, the process temperatures will be about 115° C. in the first, about 100° C. in the second, and about 90° C. in the third reactor. Even in this case a selectivity fall-off has been observed when moving from a three reactor plant to a single reactor plant. However, the selectivity of the reaction, at a 25% conversion of the starting product, proceeds from 90% by using a single reactor to about 93-95% by using three reactors in series, and therefore always shapes up higher than at the selectivity achieved by the methods of the state of the art.

It was surprisingly found that the reaction mixture leaving the oxidation phase run at the above conditions does not contain formic acid byproduct. Without wishing to be bound to any theory, it can be assumed that this is due to its further oxidation to carbon monoxide/dioxide favored by the resin.

This fact, combined with the absence of residual cations, is of the utmost importance, as it permits avoiding the washing phase needed in the processes of the known art. This leads to a considerable simplification of the process.

It was also unexpectedly seen that the pyridin resin, once separated from the reaction medium, does not require a regeneration and may therefore be reutilized for a subsequent charge. The lack of a catalyst regenerating phase contributes to the economy of the process.

As stated above, the reaction mixture leaving the oxidation reactor/s after separating from the basic medium proceeds directly to the concentrating phase, where the unreacted cumene is removed and later recycled to the oxidation reactor after adding fresh cumene. A considerable further simplification of the process derives from the fact that the concentration phase may be run in a single stage by using a thin layer concentrator (LUWA, BUSS or the like) and operating at a pressure of about 1 mm Hg and a temperature of 90° C. to 95° C. The preconcentrating phase of the known art is therefore not required, as the reaction mix does not contain the residual water originating from the washing phase in the processes of the state of the art.

Thus isolated, the cumene hydroperoxide contains a lower percentage of byproducts (acetophenone and dimethylphenylcarbinol) and, more important, does not contain any traces of cations (such as $Na^+$, $K^+$) which were, in the processes of a known art, the residual deriving from the usage of inorganic bases during the oxidation reaction. As stated before, the cumene hydroperoxide lacking residual cations can advantageously be used in the subsequent phenol synthesizing process using acidic resins as decomposition catalysts (in lieu of the sulphuric acid normally used), as the acid resins are in this case not progressively disactivated by the cations themselves.

It was further established that the process of the invention allows a drastic reduction of the dimethylphenolcarbinol byproduct. This result is extremely advantageous, because the dimethylphenolcarbinol may, unlike acetophenone, under the acidic catalysis conditions of the hydroproxide's decomposition to phenol easily generate a carbocation—by protonation of the hydroxy group and loss of a molecule of water—which may in turn react with phenol and generate byproducts (for instance α-methylstyrene or its derivatives, for instance cumylphenol).

The cumene hydroperoxide lacking inorganic cations, as obtainable by the process described above, therefore constitutes a further object of this invention.

The invention will now be further described by an example of an embodiment, outlined in the following for indicative and non-limiting purposes, with reference to the following figures.

EXPERIMENTAL PART

Figure 1:
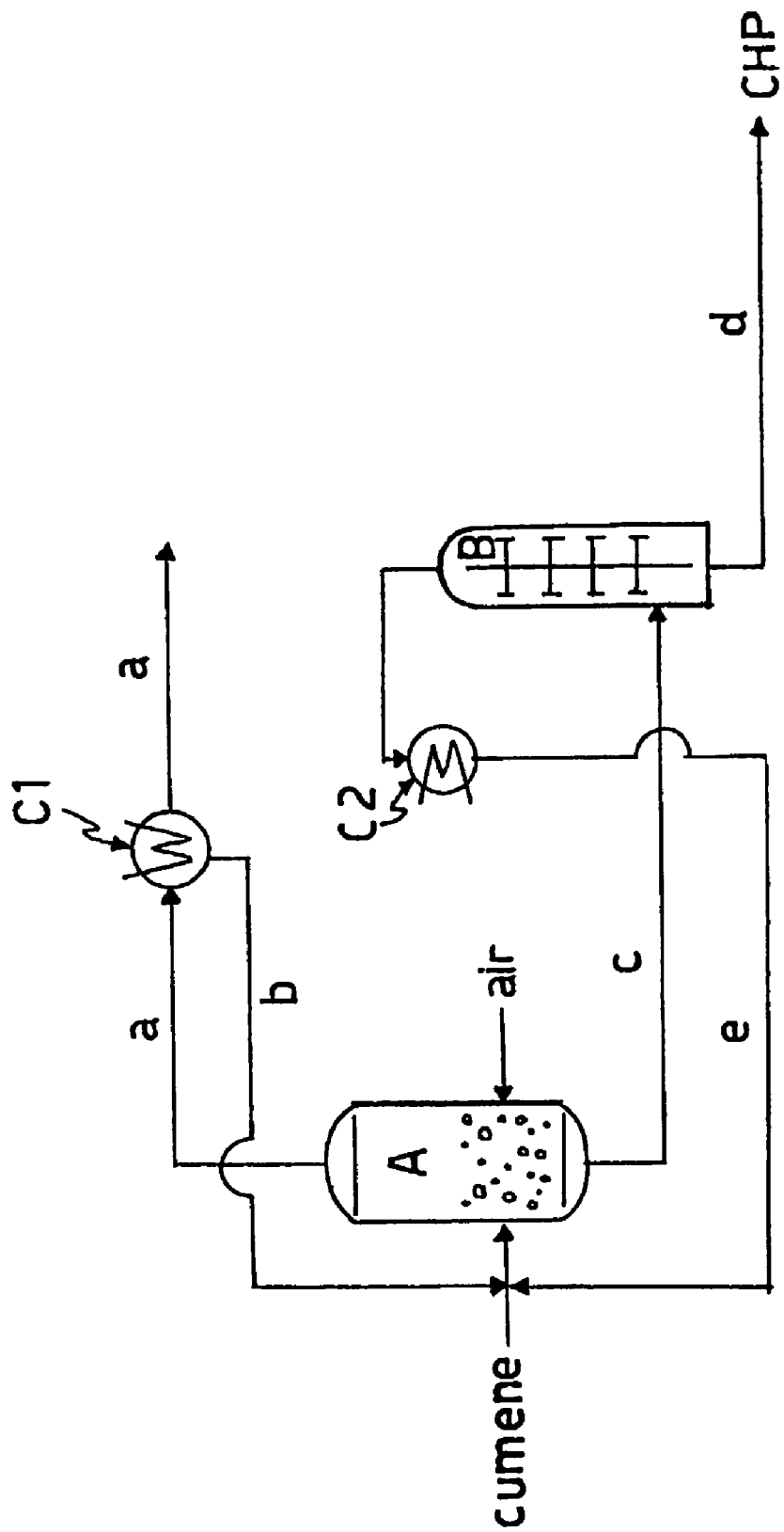
FIG. 1 shows a block diagram of a plant using an oxidation reactor for the production of cumene hydroperoxide according to the invention.

The oxidation tests were run in a "batch" fashion within a lined glass reactor of one liter volume, capable of operating up to a pressure of 12 atm and 200° C. This apparatus was fitted with a turbine stirring system capable of maintaining an optimum gas/liquid contact.

COMPARATIVE EXAMPLE

Oxidation Catalyzed by NaOH

The reactor was charged with 250 g of cumene containing a percentage of about 1-2% of cumene hydroperoxide. 280 mg of a 50% NaOH solution were also charged to the reactor. The reaction was run under stirring at 112° C. and at a pressure of 5 atm, while feeding an air flow (contaning about 20% of oxygen) of 15 Nl/hour. The reaction was extended for 240 minutes, until reaching a cumene conversion of 24.5%.

The analysis of the cumene hydroperoxide thus obtained (a colorless product) evidenced, after removing the cumene by distillation, the following main byproducts content (per 100 g of cumene hydroperoxide):

| | |
|---|---|
| dimethylphenylcarbinol** | 3.75 g |
| acetophenone** | 0.39 g |
| sodium cation* | 1.64 mg |

*determined by atomic absorption
**determined by HPLC technique

A hydroperoxide yield of 20.02% and a selectivity of 81.74% was calculated.

Example of the Invention Process—Oxidation in the Presence of Pyridinic Resins The reactor was charged with 250 g of cumene containing a cumene hydroperoxide percentage of about 1-2%. The reactor was also charged with 6 g of REILLEX™ 402 resin. The reaction was performed under agitation at 112° C. and at a pressure of 5 atm, while feeding a flow of air (containing about 20% of oxygen) at 10 Nl/hour. The reaction was extended for 360 minutes, up to a cumene conversion of 22.12%.

The analysis of the cumene hydroperoxide thus obtained (a colorless product) evidenced, after removing the cumene by distillation, the following main byproducts content (per 100 g of cumene hydroperoxide):

| | |
|---|---|
| dimethylphenylcarbinol** | 1.5 g |
| acetophenone** | 0.21 g |
| sodium cation* | untraceable |

*determined by atomic absorption
**determined by HPLC technique

A hydroperoxide yield of 20.43% and a selectivity of 92.39% was calculated.

The experimental results outlined above evidence that despite the longer time required to achieve the same degree of conversion by the process of the invention with respect to that of the known art, the resulting selectivity is nevertheless considerably improved. Moreover, the cumene hydroperoxide produced is totally lacking the cations deriving, in the process of the known art, from using a basic substance, and further exhibits about a two and a half-fold reduction in the dimethylphenylcarbinol content. On the other hand, the acetophenone byproduct is reduced by about 46%. The reduction of dimethylphenylcarbinol below the threshold value of 2% by weight is an important result achieved by the process of the invention, and the product thus produced shapes up as a preferred candidate for all the uses the cumene hydroperoxide is normally dedicated to.

A composition containing cumene hydroperoxide as a main constituent, characterized by a dimethylphenylcarbinol content of less than 2% by weight, therefore constitutes a further object of this invention. The content of dimethylphenylcarbinol will preferably be equal or lower than 1.5% by weight.

Flow Diagram of a Plant

Figure 2:
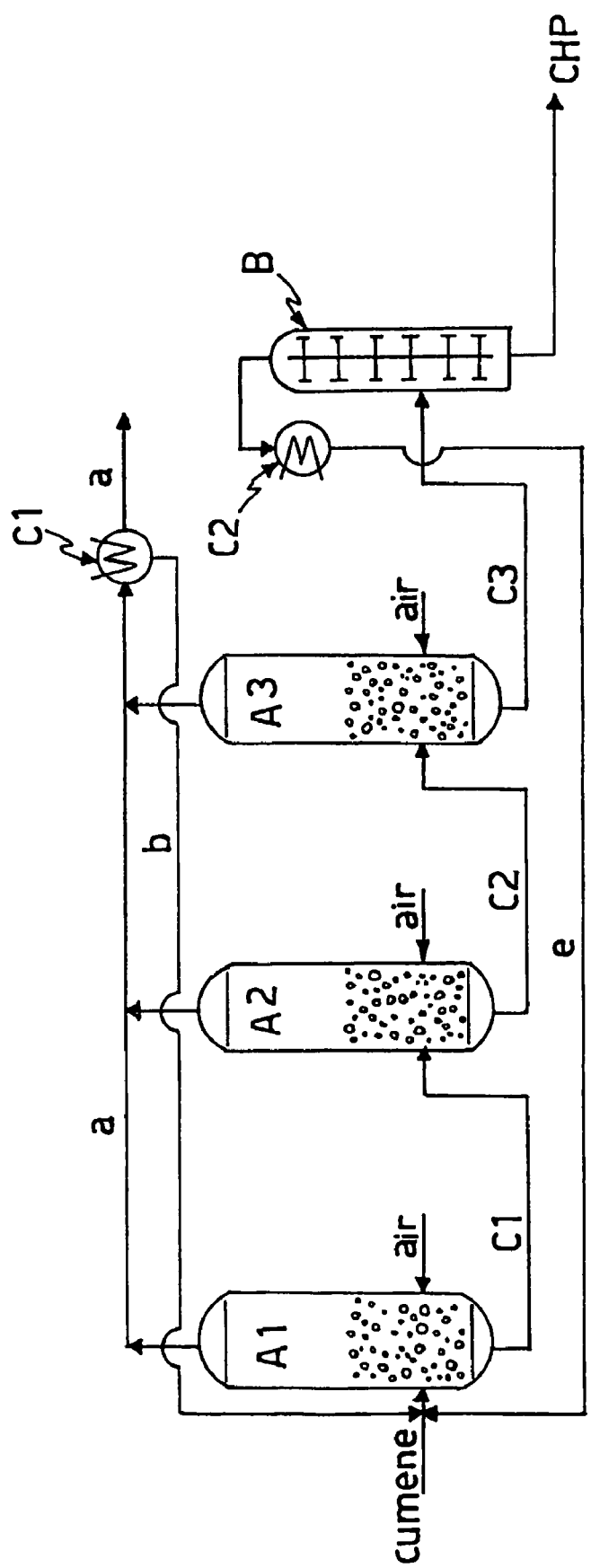
FIG. 2 shows a block diagram of a plant with three reactors in series for the production of cumene hydroperoxide according to the invention.

FIG. 1 and FIG. 2 show two possible embodiments of a plant for the synthesis of cumene hydroperoxide (CHP) according to the invention.

The flow diagrams shown in the figures are simplified in order to evidence the essential stages of the process.

FIG. 1 shows an embodiment that provides for a single oxidation reactor A, containing the appropriate quantity of basic medium in contact with the reaction environment. Cumene and air are charged to this reactor and the reaction is performed in accordance with the conditions previously outlined. The exhausted air exits at the top along the line "a" and crosses a condenser C1 in which the cumene entrained by the gaseous current is condensed and recycled to the oxidation reactor along the line "b". The exhausted air exiting from the condenser C1 is conveyed to the gaseous waste treatment before entering the atmosphere.

The reaction mixture containing cumene hydroperoxide (CHP) and unreacted cumene is transferred along the line "c" to a concentrator B, from whose top the unreacted cumene is recycled, after condensing in a condenser C2, to the oxidation reactor A along the line "e". The CHP is thus recovered at the tail end and conveyed, along the line "d", to a decomposition reactor, not shown.

The plant shown in FIG. 2 is substantially similar to that of FIG. 1, with the difference of providing three oxidation reactors A1, A2 and A3 set up in series. Each of the three reactors contains the basic medium according to the invention in contact with the reaction environment. The reaction mixture exiting the first reactor A1 is transferred along the line "c1" to the second reactor A2 and from here, after a further reaction, to the third reactor A3 along the line "c2". At this point, the reaction mixture is conveyed along the line "c3" to the concentrator B in order to separate the unreacted cumene (topside) from the CHP (tailside), which is then conveyed to the decomposition reactor (not shown).

The exhausted air exiting from the three oxidation reactors A1, A2, A3 is passed through the condenser C1 to recover the entrained cumene, and then eliminated after a decontamination treatment.

The three reactors operate at decreasing temperatures, as described above.

As can be noted from the flow diagrams shown in the figures, the process of the invention does not provide for decanting or washing phases, being conducted under substantially anhydrous conditions.

The CHP may be directly conveyed to the decomposition phase to yield phenol and acetone, or may be stored in drums or other containers of appropriate size for industrial use.

The advantages of the process of this invention are evident from the foregoing description, and have in part already been listed.

The cumene hydroperoxide free of inorganic cations obtainable by the process of the invention can advantageously be employed in a process for preparing phenol by using acidic resins.

Moreover, the use of a basic resin in the oxidation phase prevents the presence of formic acid and the use is of inorganic bases. It is consequently unnecessary to operate in a washing phase prior to the cumene hydroperoxide concentrating and isolating phase. The absence of a washing phase and therefore of a water residue in the reaction mixture in turn allows performing the concentrating step in a single low pressure stage. All this translates to a non indifferent simplification and economics of the process.

The resin need not be regenerated and this constitutes a further economic and functional advantage.

The selectivity of the formation of cumene hydroperoxide with respect to the other byproducts is superior to that of the processes of the known art, thanks to effective buffering action of the basic resin and to the fact that the formic acid cannot be traced among the byproducts of the oxidation.

It is obvious that only certain particular embodiments of the process for the production of cumene hydroperoxide have been shown as an object of this invention, which the expert in the art will be capable of supplying with all those modifications needed for adapting it to particular and contingent requirements, without thereby deviating from the scope of protection of this invention.

The invention claimed is:

1. A process for the synthesis of cumene hydroperoxide, comprising the step of oxidizing cumene to cumene hydroperoxide in a liquid phase in the presence of an oxidizing agent and of a basic resin, said basic resin being a pyridinic resin, said basic resin not releasing inorganic cations to the reaction environment.

2. A process according to claim 1, wherein the oxidizing agent is oxygen in pure form or in a mixture with other gases.

3. A process according to claim 1, wherein said cumene to cumene hydroperoxide oxidizing process is run under anhydrous conditions.

4. A process according to claim 1, where said pyridinic resin is selected from the group reticulated poly-4-vinylpyridine (a polymer of 4-ethenylpyridine with diethenylbenzene, CAS RN 9017-40-7), a high-porosity reticulated poly-4-vinylpyridine, and a polymer of 4-ethenylpyridine with diethenylbenzene and ethenylethylbenzene quaternarized with methyl chloride.

5. A process according to claim 1, wherein said basic resin is used in quantities between 0.1 g and 60 g of basic resin for each kg of cumene.

6. A process according to claim 1, wherein said oxidation, reaction is run at a temperature comprised between 60° C. and 150° C. up to the point when the conversion of the cumene to hydroperoxide is between 5% and 40%.

7. A process according to claim 6, wherein said oxidation reaction is run at temperatures comprised between 90° C. and 115° C. and for reaction times comprised between 30 minutes and 10 hours.

8. A process according to claim 1, wherein said oxidation reaction is run at relative pressures comprised in the range from 0.5 and 10 bar.

9. A process according to claim 1, wherein said oxidation reaction is run in two or more reactors in series, operating at different temperatures decreasing from the first to the last reactor.

10. A process according to claim 9, wherein the reaction temperature in said first reactor is about 115° C. and in said last reactor is about 90° C., and where the remaining oxidation reactors operate at intermediate temperatures.

11. A process according to claim 1, wherein said basic resin is contained in one or more baskets immersed in anyone of said oxidation. reactor or reactors in such a manner that said basic resin is in contact with the reaction environment.

12. A process according to claim 1, wherein said process comprises a concentrating phase of the reaction mixture exiting from said oxidizing phase for the purpose of separating unreacted cumene from the cumene hydroperoxide product.

13. A process according to claim 12, wherein said concentrating phase is operated in a direct succession to said oxidizing phase.

14. A process, comprising: synthesizing cumene hydroperoxide according to claim 1 and decomposing the cumene hydroperoxide to form phenol and acetone.

* * * * *